United States Patent [19]

Anderson et al.

[11] Patent Number: 5,314,830
[45] Date of Patent: May 24, 1994

[54] IMMOBILIZED HYDROPHOBICALLY-MODIFIED ANTIBODIES

[75] Inventors: William L. Anderson; Dennis Otero, both of Albuquerque, N. Mex.

[73] Assignee: University of New Mexico, Albuquerque, N. Mex.

[21] Appl. No.: 968,076

[22] Filed: Oct. 30, 1992

[51] Int. Cl.$^5$ ............... G01N 33/552; G01N 33/531; C07K 15/28; C07K 17/00
[52] U.S. Cl. .................. 436/524; 436/527; 530/391.1; 530/391.9; 435/7.1
[58] Field of Search ............ 530/391.1, 391.9; 436/532, 547, 524, 527; 435/7.1, 181

[56] References Cited

U.S. PATENT DOCUMENTS

| | | | |
|---|---|---|---|
| 4,735,906 | 4/1988 | Bastiaans | 436/501 |
| 4,808,530 | 2/1989 | Means et al. | 435/177 |
| 4,952,519 | 8/1990 | Lau | 435/815 |
| 5,059,654 | 10/1991 | Hou et al. | 422/70 |

OTHER PUBLICATIONS

Anderson, et al.; Journal of Immunological Methods, vol. 109, No. 1, pp. 37–42; 1988.
Shons, A. (1972). Immunoassay with coated piezoelectric crystals. J. Biomed. Materl. Res. 6: 565–570.
D'Souza, S. F., Melo J. S., Deshpande, A., and Nadkarni, G. (1986). Immobilization on yeast cells by adhesion to glass surfaces using polyethyleneimine. Biotech. Lett. 8:643–648.
Blanchard, G. C., Taylor, C. G., Busey, B. R., and Williamson, M. L. (1990). Regeneration of immunosorbent surfaces used in chemical, industrial and environmental biosensors. Role of covalent and non-covalent interactions. J. Immunol. Methods 130: 263–275.
Boitieux, J. L., Desmet, G., Wilson G. and Thomas, D. (1990). The specific immobilization of antibody fragments on membrane for the development of multifunctional biosensors. Ann. N.Y. Acad. Sci. 613: 391–395.
Guilbault, G. G., Loung, J. H. T., Prusak-Sochaczewski, E. (1989). Immobilization methods for piezoelectric biosensors. BioTechnology 7: 349–351.
Loung, J. H. T., Prusak-Sochaczewski, E., and Guilbault, G. G. (1990). Development of a piezoimmunosensor for the detection of *Salmonella typhimurium*. Ann N.Y. Acad. Sci. 613: 439–443.
Muramatsu, H., Dicks, J. M., Tamiya, E. and Karube, I. (1987). Piezoelectric crystal biosensor modified with protein A for determination of immunoglobulins. Anal. Chem. 59: 2760–2763.
Rajakovic, L., Ghaemmaghami, V., and Thompson, M. (1989). Adsorption on film-free and antibody-coated piezoelectric sensors. Anal. Chim. Acta 217: 111–121.
Roederer, J. E. and Bastiass, G. J. (1983). Microgravimetric immunoassay with piezoelectric crystals. Anal. Chem. 55: 2333–2336.
Suleiman, A. A., and Guibault, G. G. (1991). Piezoelectic Immunosensors and their applications. Anal. Lett. 24: 1283–1292.
Sutherland, R. M., Dahne, C., Place, J. F., and Ringrose, A. S. (1984). Optical detection of antigen-antibody reactions at a glass-liquid surface. Clin. Chem. 30: 1533–1538.

*Primary Examiner*—George C. Elliott
*Attorney, Agent, or Firm*—Hoffman, Wasson & Gitler

[57] ABSTRACT

The invention comprises stable, antigen-sensitive surfaces containing immobilized antibody modified with a polyethylene glycol spacer arm including a terminal hydrophobic moiety. The surfaces are generally useful in immunoassay procedures, especially microgravimetric assays such as those employing antibody immobilized on piezoelectric crystal surfaces.

24 Claims, 5 Drawing Sheets

IMMOBILIZED HYDROPHOBICALLY-MODIFIED ANTIBODIES

BACKGROUND OF THE INVENTION

1. Field of the Invention

New detection methods for immunoassays which allow the assays to be performed rapidly with a minimum amount of equipment and operator time have been recently reported. In several of these procedures, immune complexes are identified directly, without the use of fluorescent, radiochemical or enzyme labeling methods. These label-independent methods detect immune complex formation based on electrochemistry (*Electrochemical Sensors in Immunological Analysis*, Ngo, TT ed. Plenum Press, NY N.Y. USA), ellipsometry (*J. Colloid Interface Sci.* 111:544–554, 1986), optical wave guidance (*Sensors Actuators B*1:592–596, 1990), surface plasmon resonance (*Biosensors* 3:211–225, 1988, *Z. Phys.* 4:299–304, 1983; *Biotechniques* 11:620–627, 1991), and the piezoelectric effect (*Biosensors Bioelectron* 5:13–26, 1990; *Anal. Chem. Acta* 271:111–121, 1989; *Anal. Chem.* 55:2333–2386, 1983; *Science* 249:1000–1007, 1990). In spite of obvious advantages for rapid, label-independent biospecific analysis, all of the procedures share the disadvantage of requiring immobilized antibody or antigen. Conventional procedures for preparing such immunoreactive surfaces are not optimal, and newer methods for coupling antibody to solid surfaces have been reported (*Ann.N.Y. Acad. Sci.* 613:391–395; 439–443, 1990).

2. Description of Related Art

Coating techniques currently in use to prepare immunoreactive surfaces include entrapment of the antibody onto a polymer coated surface (*Biotech Letts* 8:643–648, 1986), glutaraldehyde crosslinking of antibody onto surfaces (*J. Biomed. Mater. Res.* 6:565–570, 1970, *Clin. Chem.* 30:1533–1538, 1984), absorption of antibody onto silanated surfaces (*Anal. Chem.* 55:2333–2336, 1983), and attachment of antibody to immobilized protein A (*Anal. Chem.* 59:2760, 1987). These methods, however, generally have the common drawback that each antibody coated surface can be used only a limited number of times before immunoreactivity is lost (see, e.g., *Anal. Lett.* 24:1283–1292, 1991; *Biotechnology* 7:349–351, 1989; *Ann. N.Y. Acad. Sci.* 613:439–443, 1990).

SUMMARY OF THE DISCLOSURE

The invention provides a method for immobilization of antibody for use in immunoassay procedures, comprising adsorption of antibody covalently modified with a hydrophobic moiety onto a suitable surface. The method is particularly useful in label-independent assays of the type described supra, employing for example piezoelectric crystals as the immobilizing surface, but is also useful in traditional label-dependent assays employing, for example, glass beads or silica crystals as support.

In order to achieve adequate hydrophobicity of the reactive surface, the hydrophobic moieties, such as fatty acid residues, are linked to the antibody via a water-soluble polymer, preferably polyethylene glycol or a derivative thereof, which permits extensive antibody modification with the selected hydrophobic moiety without significant loss of antigen-binding activity.

The antibody-modified surfaces of the invention are stable and reusable for several assays. They are easily prepared, requiring no priming or intermediate coating of the base surface. In particular, they are comparable in antigen-sensitivity to surfaces coated with unmodified antibody. Additionally, there is reduced variation between individual coated surfaces. Piezoelectric immunoreactive surfaces prepared with stearyl poly(ethylene glycol) (SPEG) modified antibody can undergo twenty or more cycles of antigen addition and removal without substantial loss of binding activity, with detectable frequency changes routinely observable at nanomolar antigen concentrations. Total analysis time is on the order of a few minutes, with demonstrated reproducibility between replicate analyses.

DETAILED DESCRIPTION OF THE INVENTION

Figure 1:
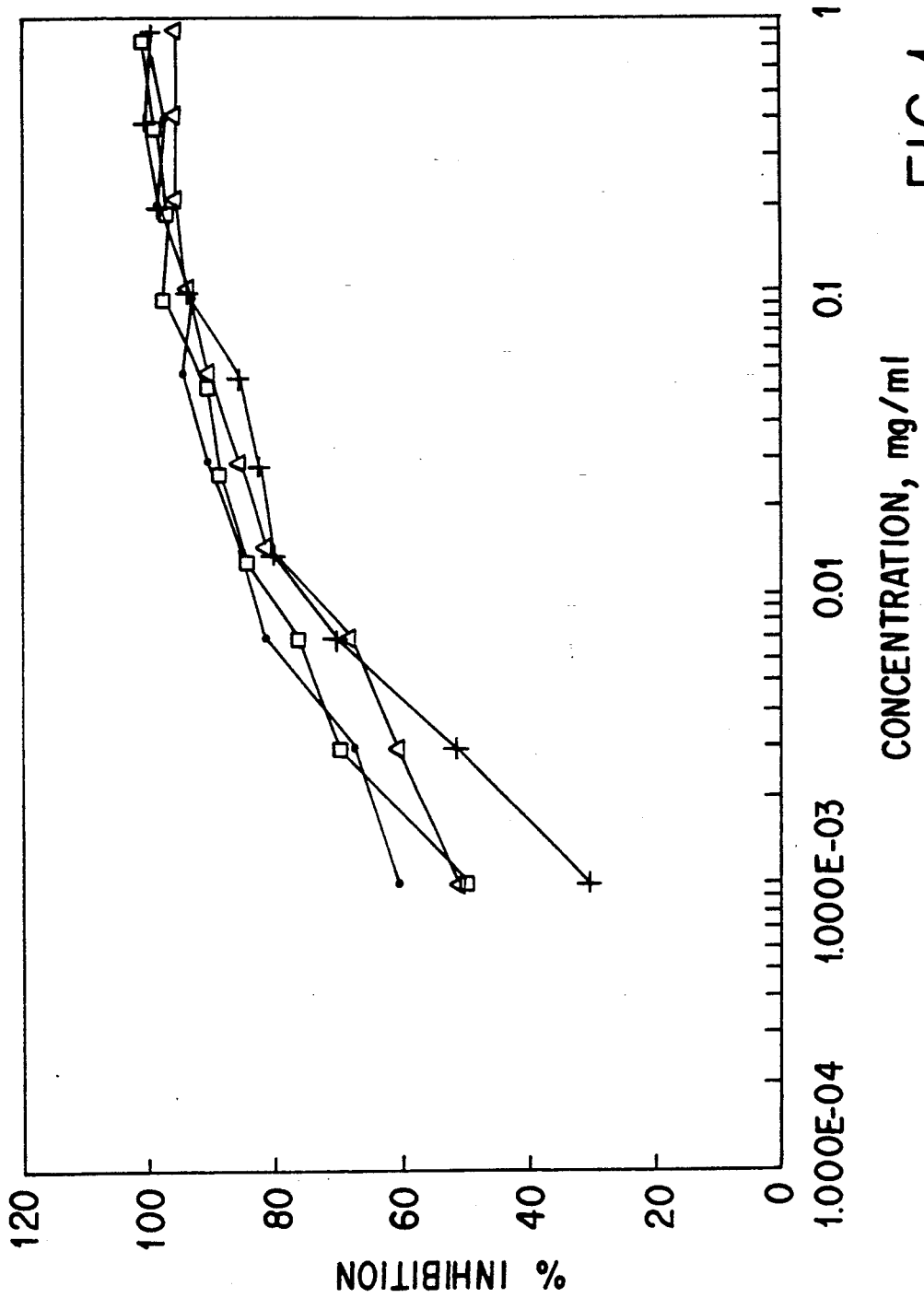
FIG. 1: Competitive inhibition enzyme immunoassay of sPEG modified goat anti-murine IgG. The ability of either sPEG-modified or unmodified antibody to inhibit the binding of an alkaline phosphatase labeled goat anti-murine IgG antibody to antigen coated micro EIA plates is represented in this figure. The solid circles indicate unmodified antibody. The Cross indicates antibody that had 12% of available lysine residues modified; Square, 19% and Triangle, 47%. No inhibition is observed for control sPEG-modified antibody.

While the invention is discussed in terms of antibody immobilization, the procedures described are readily adaptable by those skilled in the art to immobilization of other proteins such as antigens or enzymes for use in known detection or separation procedures.

In accordance with the invention polyethylene glycol or a derivative thereof (herein referred to as PEG) carrying a hydrophobic moiety is covalently bound to the antibody to be used in the immunoreaction. Methods for attaching PEG to antibody or other protein are known in the art. Modification of antibody with PEG employing a tresyl ester intermediate is described herein; methods employing active ester or secondary amine intermediates have been described in the art (see, e.g., *J. Immunol. Methods* 109:37–42, 1988 and U.S. Pat. No. 4,732,863 to Tomasi, et al, issued March 1987, incorporated herein by reference). Any suitable method which does not contribute significantly to denaturation of the antibody or other protein, or otherwise adversely affect the intended application can be used. PEG modification of from about 15 to 50% of an antibody's available lysine residues is suitable for purposes of the invention, depending on the hydrophobic moiety employed; the PEG addition should not be so great as to substantially decrease antigen binding activity of the modified antibody. For optimum stability for repeated use, a degree of modification at the lower end of this range, about 15% to 25%, is often preferable.

While other water-soluble polymers can be substituted, polyethylene glycol is preferably employed for its neutrality under assay conditions and ease of reaction with sensitive proteins. Polymers of a molecular weight of about 50 to about 150 are preferred, particularly of about 80 to 90, as such polymers permit both a high degree of antibody modification with the PEG hydrophobic moiety and retention the hydrophobic moiety sufficiently close to the coated surface for optimum efficiency.

Hydrophobic moieties for antibody attachment via the PEG linker arm or spacer can be any suitable moiety having hydrophobic properties which does not adversely affect the critical biological properties of the immobilized protein or the assay system. Fatty acid residues (e.g., $C_{16-18}$) are exemplary, and a PEG/-stearyl/alcohol adduct is illustrated herein as a useful, commercially available intermediate. PEG is conveniently modified with the chosen hydrophobic moiety according to known chemical principles prior to modification of the antibody.

The modified antibody carrying the hydrophobic moiety is adsorbed onto a receptive surface as known in the art for immobilization of unmodified antibody. Although non-covalent interactions hold the antibodies to the surface, the antibody-coated surfaces of the invention are durable, and can be reused several times. The piezoelectric surfaces used herein were selected because they allow the rapid, sensitive, inexpensive detection of immunoreactions using label-independent methods; however, the modified antibodies of the invention can be adsorbed onto any other suitable surface of the type known in the art, typically microporous mineral bodies such as glass beads, silica crystals, ceramics, or optical fibers.

The immobilized antibodies are then used in a conventional manner in immunoassay procedures for determination or detection of antigen. Surfaces bound with other proteins according to the invention are similarly used in comparable protein separation/detection/determination assay procedures, as known in the art. For example, as previously noted, antigen rather than antibody is readily immobilized according to the methods of the invention to prepare the immunoreactive surface.

EXAMPLES

I. Antibody Purification

For primary immunizations, 500 ug of mouse IgG (Sigma Co., St. Louis, Mo., USA), emulsified in complete Freunds adjuvant, was injected at multiple sites (100 ul/site) into goats. For secondary and subsequent immunizations, the antigen was emulsified in incomplete adjuvant and no more than 100 ul was injected per site. Only high titered late course antisera was used for the purification of antibodies studied in all subsequent experiments. The antibody was purified by affinity chromatography on mouse IgG immobilized on CM-BioGel A 1.5 m (Bio Rad Laboratories, Richmond, Calif., USA) using the carbodiimide coupling procedure described in BioRad Technical Bulletin, 79–0457 Richmond, Calif. Following application of the antisera to the affinity column, the column was washed with 0.5M NaCl buffered with 0.02M sodium phosphate, pH 7.2, until no further protein was eluted. The specific antibody was removed by elution with 3.5M NaSCN and the chaotropic agent removed and antibody sample concentrated by vacuum dialysis.

II. Activation of stearyl-PEG-OH

Samples of PEG modified with stearyl alcohol (sPEG-OH) on of the polymer chain were purchased commercially (Sigma Chemical Co., St. Louis, Mo., USA). Preliminary experiments evaluating the effect of PEG size suggested that PEG with a molecular weight of 88 was optimal for these experiments and consequently that size EPG was used. The sPEG-OH was dissolved in a Benzene:Pyridine mixture (80:20) and dried over Molecular Sieve 3A (Matheson Coleman and Bell, Norwood, Ohio, USA). A two-fold molar excess of 2,2,2-trifluoroethanesulfonyl chloride (Aldrich, Milwaukee, Wis., USA) was slowly added to the polymer solution and the reaction was allowed to proceed for 30 min. at room temperature. The trifluoroethylsulfonate ester of sPEG-OH was isolated by precipitation with cold petroleum ether. The sPEG-tresyl ester product was then redissolved in dry benzene and again precipitated with petroleum ether. The sPEG-tresyl ester was stored dry under nitrogen at 4°.

III. Antibody modification with sPEG-tresyl ester

The sPEG-tresyl ester was dissolved in dry methylene chloride and this solution was used to coat the walls of the reaction vessel. Antibody at 2 mg/ml in 0.5M NaHCO$_2$ was added to the reaction vessel, with mixing to redissolve the sPEG-tresyl ester. The extent of antibody modification was controlled by varying the ratio of sPEG-tresyl ester to antibody in the reaction mixture. Following an overnight incubation at 4° the antibody was purified by dialysis against phosphate buffered saline (PBS) using 50,000 molecular weight cut off dialysis tubing. The protein concentration was determined by the 4,4'-dicarboxy-2,2'-biquinoline method of Smith (*Anal. Biochem.* 150:76–85, 1985). The extent of antibody modification was determined using the fluorescamine reaction with primary amino groups as described by Stocks, et al (*Anal. Biochem.* 154:232, 1986). Percent antibody modification is defined as the percentage loss of fluorescamine reaction amino groups following the modification procedure.

IV. Evaluation of antigen binding activity

The antigen binding activity of spEG-modified and unmodified goat anti-mouse IgG was evaluated in competitive inhibition enzyme linked assays. For this assay, an aliquot of affinity purified antibody was coupled to calf intestine alkaline phosphatase (Sigma Chemical Co., St. Louis, Mo., USA) (1000 IU/mg) as described by Avrameas (*Immunochemistry* 6:48, 1969). Prior to use in the assay, each enzyme linked reagent was titrated for binding activity by incubating several concentrations of the conjugate for 2.5 hours on micro-EIA plates (Vangard International, Inc., Neptune, N.J., USA) which had been previously coated, for 18 hours, with either the relevant antigen or irrelevant control protein at 10 ug/ml in 0.05M $NaHCO_2$. Following the incubation, nonbound enzyme conjugate was washed off the plates with distilled water and the amount of bound enzyme was evaluated by measuring the hydrolysis of p-nitrophenyl phosphate (Sigma Chemical Co.) at pH 10. From this experiment the amount of conjugate necessary to 90% saturate the plate was determined and this concentration of conjugate was used in subsequent experiments. To evaluate antigen binding activity of modified antibodies, the predetermined amount of antibody-enzyme conjugate was incubated with serial dilutions of either sPEG-modified or unmodified antibody on either antigen coated plates or plates coated with an irrelevant protein. Following a 2.5 hr. reaction period, the plates were washed and enzyme content determined by measuring hydrolysis of p-nitro-phenyl phosphate. Losses in binding activity was evaluated by comparing inhibition curves for both modified and unmodified antibody. In all cases, the antigen binding activity of modified antibody was compared to the unmodified molecule.

V. Preparation of the piezoelectric surface

Ten MHz piezoelectric quartz crystals (Crystek Corporation, Ft. Meyers, Fla., USA) were coated with the goat anti-mouse IgG antibody by either absorption of the sPEG-modified antibody or by glutaraldehyde cross linking of the antibody to primary amine modified crystals.

A. To prepare the crystal surface for glutaraldehyde modification, the crystals were initially treated with a 2% solution of 3-aminopropyltriethoxysilane (Sigma Chemical Co., St. Louis, Mo., USA) and incubated overnight at 45° C. Following the amine modification, a 25% solution of glutaraldehyde was added to the surface. After 10 minutes, the crystal surface was washed with water and a 2 mg/ml solution of affinity purified antibody was added to the crystal. The crystal was then washed with water and air dried. The antibody coated crystals were stored dry at room temperature.

B. To coat piezoelectric surfaces with sPEG-modified antibody, a 2 mg/ml solution of modified antibody was air dried onto the crystal surface. The antibody coated crystals were stored dry at room temperature. Prior to being used in each test, crystals prepared by both methods were initially soaked, for 3 minutes, in a 3.5M solution of NaSCN, buffered at pH 7.4 with 0.02M sodium phosphate buffer to remove loosely bound materials.

VI. Frequency response of antibody coated piezoelectric crystals

Following incubation of the antibody coated crystal under the experimental conditions, the crystals were washed with water and air dried. The frequency response of the crystal was determined in a Pierce oscillator circuit. In all cases, the frequency response of the crystal was determined prior to the experimental condition, following antigen exposure and again after removal of the bound antigen by washing with 3.5M NaSCN. The data points in each experiment are the average of five determinations. Each experiment was repeated at least three times.

VII. Results

The effect of sPEG modification on the antigen binding activity of goat anti-mouse IgG was determined using competitive inhibition enzyme linked immunoassays. The results of a typical determination for antibody samples where the level of sPEG modification varies between 0 and 47% is shown in FIG. 1. The results displayed in this figure show no loss in antigen binding activity at all levels of modification tested. No antigen binding activity could be observed for control goat IgG either with or without sPEG-modification. These results demonstrate that the sPEG modification does not destroy antigen binding activity even at relatively high levels of modification.

Figure 2:
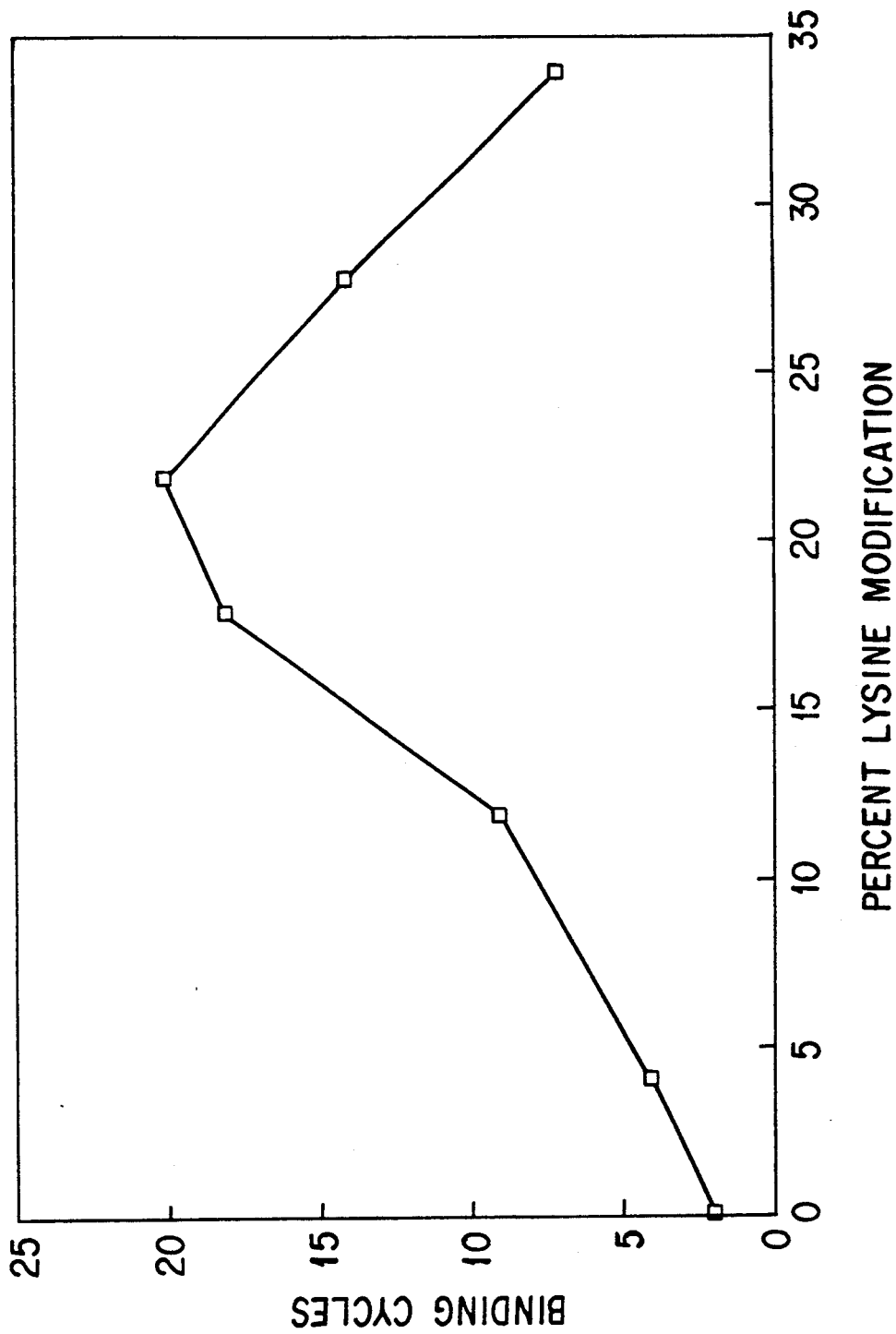
FIG. 2: Effect of extent of lysine modification on the number of times antigen can be successfully bound to and removed from piezoelectric crystals using the sPEG method. Antibody coated crystals were incubated with antigen for 10 minutes and antigen was removed from the crystal by a 3.0 minute wash in 3.5 M NaSCN.

To evaluate the optimal level of antibody modification with sPEG, for coating piezoelectric quartz crystals, a series of piezoelectric crystals were treated with identical concentrations of sPEG-modified goat anti-mouse IgG. In this set of experiments the extent of antibody modification varied from 0 to 34% of available lysine residues modified. The antigen binding activity of all modified samples was indistinguishable from the unmodified antibody in the competitive inhibition enzyme immunoassay. These crystals were then tested to evaluate the number of times that antigen could be successfully bound to and removed from the crystals. The results of this test (FIG. 2) show that antibody with 20% of the lysine residues sPEG-modified are the most stable to repeated uses on piezoelectric surfaces. Under conditions of either more or less extensive modification, the coated surfaces could not go through as many cycles of antigen addition or removal.

Figure 3:
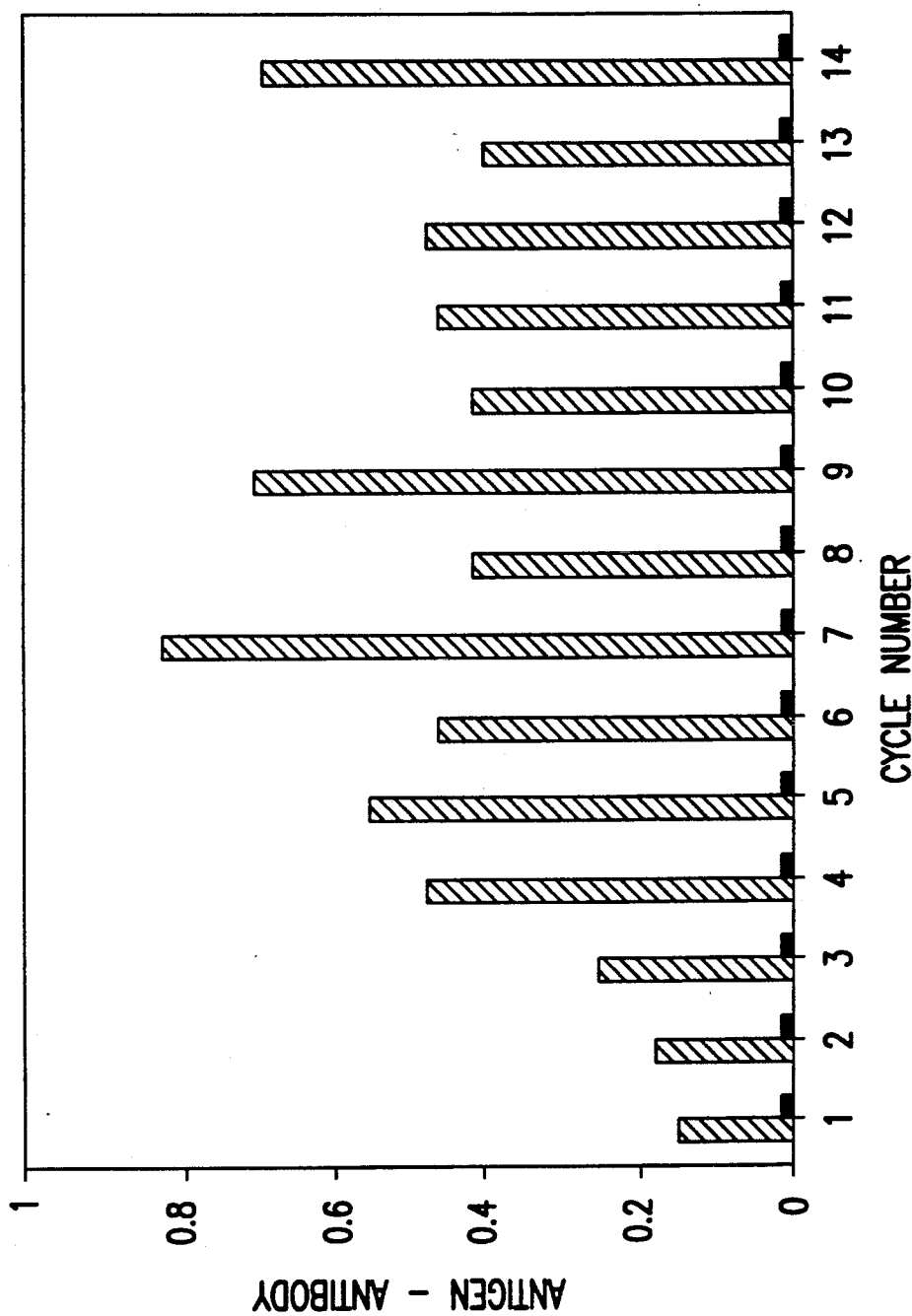
FIG. 3: Antigenic specificity of piezoelectric crystals following coating with sPEG-modified goat anti-murine IgG. The crystals were incubated in either murine IgG (hatched bar) or hen egg conalbumin (solid bar) for 10 minutes. The ratio of antigen binding to antibody on the crystal is indicated on the ordinate. The antigen binding to each crystal was followed over 14 cycles of antigen addition and removal.

An example of the response observed for a single antibody coated crystal during the antigen addition and removal cycles is shown in FIG. 3. The antibody used in this test had 18% of its lysine amino groups modified with sPEG. The data is presented by comparing the ratio of antigen bound per antibody on the crystal in consecutive antigen binding cycles. These data show that the saturation of antibody on the crystal surface is low during the first few cycles. Since the frequency response of the crystal following 3.5M NaSCN treatment generally rises during these initial antigen binding trials, it suggests that this low response on initial trials is due to the removal of loosely adhered antibody. Following these initial cycles of antigen binding a more stable response is observed where approximately 40% of the surface bound antibody is capable of binding antigen. These data also show that for some individual trials, inordinately high results can be observed. Since the data reported is calculated from the difference between the crystal response to a control protein (hen egg conalbumin) and the specific antigen, all the error in the two measurements appears in the response to the antigen.

The characteristics of antibody coated piezoelectric crystals prepared using either the glutaraldehyde method or the sPEG method are compared in Table 1. From this table it appears that antibody coated crystals prepared by both methods are equally sensitive, showing an average maximum frequency change to saturating antigen conditions of approximately 150 Hz. However, the reproducibility between replicate analyses for crystals prepared using these two different protocols is very different. The standard deviation of replicate analyses for the glutaraldehyde prepared crystal is almost three times as large as that observed for the sPEG prepared crystal. In addition, the number of times antigen can be successfully bound to the crystal and then removed was significantly greater for the sPEG prepared crystal $(19+1-2)$ than for the glutaraldehyde prepared crystal $(6\pm3)$.

The consistency in preparing individual piezoelectric crystals is evaluated in Table 2. This table reports the reproducibility between antibody bound and maximum antigen response for 10 individual piezoelectric crystals prepared sequentially using 28% sPEG-modified goat antibody. The mass of both antibody and antigen bound to the crystal is reported during the frequency shift in Hz. The variability in antibody coating between individual crystals is approximately 10%. The size of this error appears to be due to a few crystals with either high or low coating levels. On average 23% of the antibody on each crystal is capable of binding antigen. The data in FIG. 3 was obtained using antibody that was 18% modified while a 28% modified antibody was used in Table 2. It is apparent from this figure that antibody coated crystals that have either significantly higher or lower levels of antibody attached to the crystal also have levels of antigen saturation that are much different from the average. Accordingly, for maximum reproducibility both the percent antibody modification and the crystal coating density should be well controlled, and selection criteria relating to crystal response and coating density should be established for individual applications.

TABLE 1

COMPARISON OF sPEG AND GLUTARALDEHYDE METHODS FOR PREPARING ANTIBODY COATED SURFACES

| | METHOD | |
|---|---|---|
| | sPEG | Glutaraldehyde |
| Average number of uses (mean +/− standard deviation) | 19 +/− 2 | 6 +/− 3 |
| Frequency Response to 3.3 nM murine IgG (Hz) (mean +/− standard deviation) | 180 +/−45 | 149 +/−125 |

TABLE 2

REPRODUCIBILITY BETWEEN ANTIBODY COATED PIEZOELECTRIC CRYSTALS USING THE sPEG METHOD

| | (Frequency Shift in $H_2$) | | |
|---|---|---|---|
| CRYSTAL NUMBER | ANTIBODY BOUND CRYSTAL | ANTIGEN BOUND CRYSTAL | ANTIGEN ANTIBODY |
| 1 | 691 | 70 | 10 |
| 2 | 344 | 111 | 32 |
| 3 | 657 | 141 | 21 |
| 4 | 511 | 155 | 30 |
| 5 | 415 | 135 | 33 |
| 6 | 249 | 87 | 35 |
| 7 | 500 | 108 | 22 |
| 8 | 535 | 105 | 20 |
| 9 | 526 | 113 | 21 |
| 10 | 539 | 105 | 19 |
| AVERAGE | 497 | 113 | 23 |
| std. error | 42 | 8 | |

Figure 4:
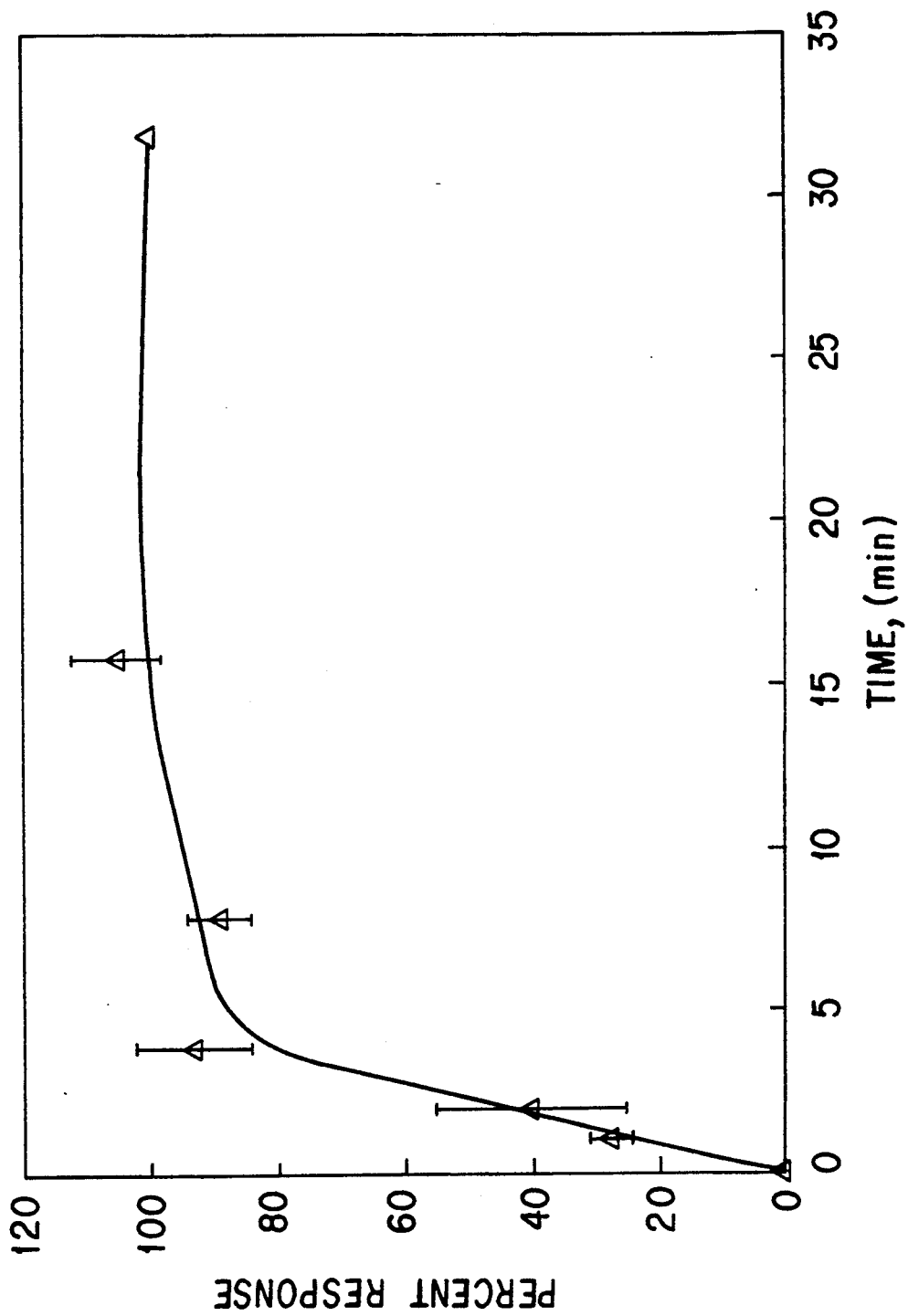
FIG. 4: Rate of murine IgG reaction, with piezoelectric crystals prepared using sPEG-modified goat anti-murine IgG. Modified crystals were incubated in a 3.3 nM solution of antigen for the times indicated on the abscissa. Each test was performed five times and the error bars represent the standard deviation. No response was observed for control antigen.

The rate of antigen reaction with antibody modified piezoelectric crystals is shown in FIG. 4. These data show that the reaction of a polymeric antigen with the surface, although much slower than solution reactions, still proceeds at a significant rate. The reaction is essentially complete in 5 minutes. The amount of antigen deposited on the surface remains stable for at least another 25 minutes.

Figure 5:
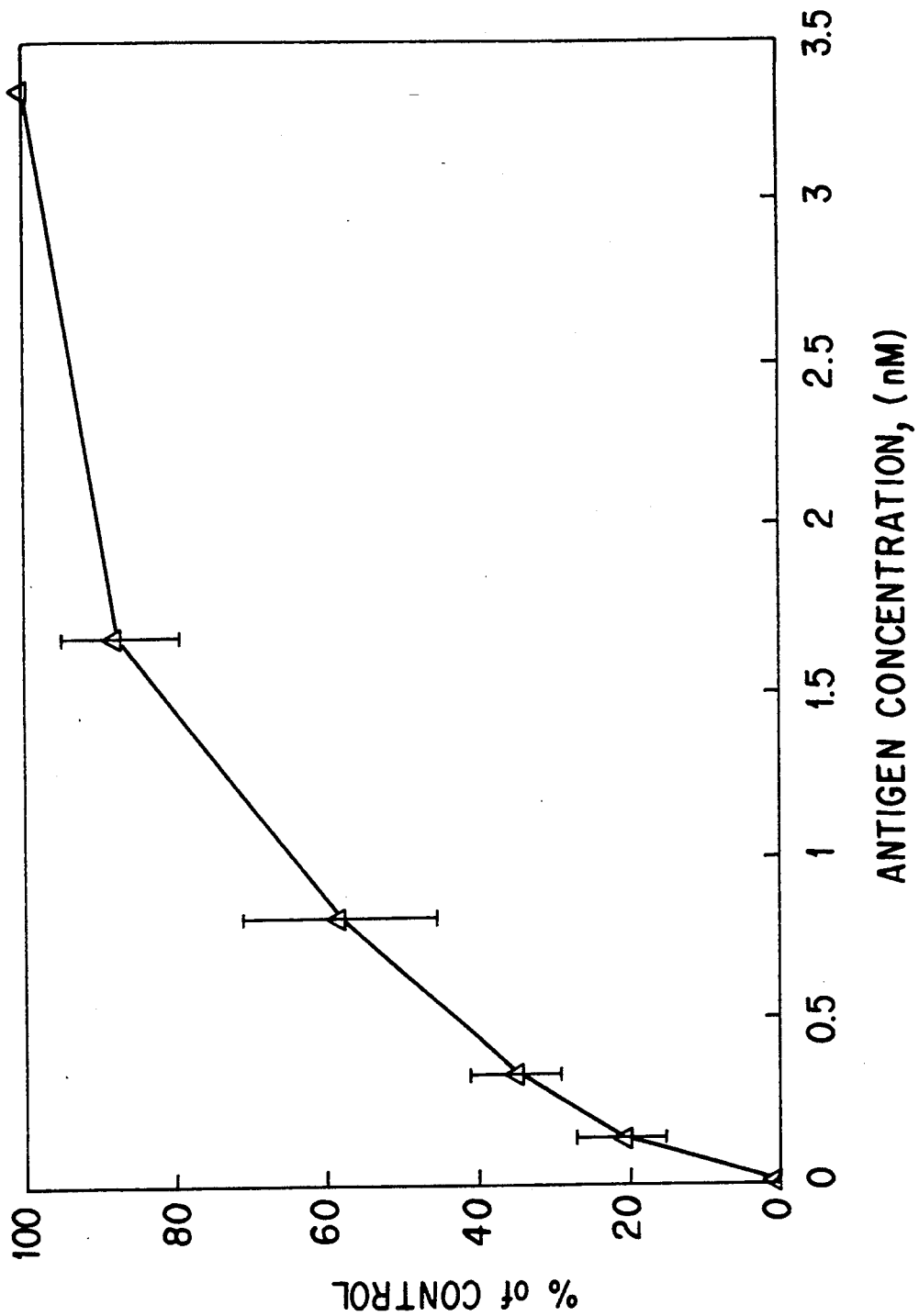
FIG. 5: Effect of murine IgG concentration on the frequency shift of piezoelectric crystals coated with sPEG-modified goat anti-murine IgG. Antigen, at the concentration indicated on the abscissa, was incubated for 10 minutes with the modified crystal. The frequency response was determined and compared to the 3.3 nM standard. Each test was performed five times and the error bars indicate the standard deviation of the data.

FIG. 5 illustrates the sensitivity of the antibody coated crystal response to antigen concentration. In this experiment, the antibody coated crystals were incubated in an antigen solution for 10.0 minutes. Under these conditions a very narrow dose response curve is observed between antigen concentrations of 0 and 3 nM. At concentrations above 3.3 nM, no additional change in frequency response was observed.

The non-covalent attachment method described herein produces a surface antibody that is stable to approximately 20 cycles of antigen addition and removal. The mechanism of failure after 18–20 repeated uses is not known and may be related to denaturation caused by the repeated exposure to chaotropic agents rather than dissociation of sPEG-modified antibody from the crystal surface. Only one method was used for the removal of antigen from the surface in these studies, although it is contemplated that dissociating agents other than 3.5M NaSCN will function equally well or better/see, e.g., *J. Immunological Methods* 130:263–275, 1990).

The data demonstrates that antigen reaction with antibody coated surface is essentially complete within 5 minutes when saturating concentrations of antigen are used. Nygren et al (*J. Immunol. Methods* 85:87–95, 1985) evaluated the dissociation time of antigen antibody reactions on surfaces and found extremely slow dissociation rates for both bivalent and monovalent antibodies. These results suggest the surface reactions reported herein may not have come to equilibrium. Consequently, the dose response curve presented in FIG. 5 may be dependent upon the time that the surface is in contact with the antigen-containing solution. Therefore, with longer incubation time, increased sensitivity may be achieved. Under the conditions used, 1 nM concentrations of protein antigen can be detected. There is, however, a very narrow dose-response curve with the crystals being saturated by 3.3 nM concentrations of mouse IpG antigen, and it is potentially possible to increase the size of this curve by increasing the surface area of the piezoelectric crystal.

What is claimed is:

1. A protein modified with a hydrophobic moiety attached to the protein by a spacer comprising a water-soluble polymer, directly adsorbed onto an unprimed microporous mineral body surface.

2. The modified protein of claim 1, wherein the protein is an antibody or antigen.

3. The modified protein of claim 2, wherein the water-soluble polymer is polyethylene glycol or a derivative thereof.

4. The antibody or antigen of claim 3, wherein the hydrophobic moiety is a fatty acid residue.

5. The antibody or antigen of claim 4, wherein the fatty acid residue contains from 16 to 18 carbon atoms.

6. The antibody or antigen of claim 4, wherein the hydrophobic moiety is stearyl.

7. The antibody or antigen of claim 2, wherein the surface is a piezoelectric crystal surface.

8. The antibody or antigen of claim 7, wherein the water-soluble polymer is polyethylene glycyol or a derivative thereof.

9. The antibody or antigen of claim 7, wherein the hydrophobic moiety is a fatty acid residue.

10. The antibody or antigen of claim 7, wherein the hydrophobic moiety is a fatty acid residue and the water-soluble polymer is polyethylene glycol or a derivative thereof.

11. The antibody or antigen of claim 10, wherein the polyethylene glycol has a molecular weight of from about 50 to 150.

12. The antibody or antigen of claim 11, wherein the polyethylene glycol has a molecular weight of from about 80 to 90.

13. The antibody or antigen or claim 11, wherein the polymer has a molecular weight from about 80 to 90.

14. The modified protein of claim 1, wherein the surface is a glass bead surface, a silica crystal surface, a ceramic surface, an optical fiber surface or a quartz surface.

15. The modified protein of claim 14, wherein the surface is a piezoelectric quartz crystal.

16. The modified protein of claim 15, wherein the protein is an antibody or antigen.

17. The modified protein of claim 16, wherein the water-soluble polymer is polyethylene glycol or a derivative thereof.

18. The antibody or antigen of claim 17, wherein the hydrophobic moiety is a fatty acid residue.

19. The modified protein of claim 18, wherein from about 15 to about 25% of the lysine residues of the antibody are substituted with polyethylene glycol or a derivative thereof.

20. The modified protein of claim 18, wherein the protein is adsorbed upon the surface by application to the surface followed by air drying.

21. A method for preparing an immunoreactive surface, comprising coating an unprimed microporous mineral body surface with an antigen or antibody modified with a hydrophobic moiety attached to the antigen or antibody by a spacer comprising a water-soluble polymer by drying the modified antigen or antibody onto the unprimed surface.

22. The method of claim 21, wherein the microporous mineral body surface is a piezoelectric crystal surface.

23. The method of claim 22, wherein the water-soluble polymer is polyethylene glycol having a molecular weight of from about 50 to 150.

24. The method of claim 23, wherein the hydrophobic moiety is a fatty acid residue.

* * * * *